United States Patent
Moran et al.

(10) Patent No.: US 9,759,712 B2
(45) Date of Patent: Sep. 12, 2017

(54) METHOD FOR COLLECTING MEDICAL DATA AND ASSOCIATED SYSTEM

(71) Applicant: GLUCOME LTD., Yarkona (IL)

(72) Inventors: Dov Moran, Kfar Saba (IL); Roee Tuval, Ramat Hasharon (IL); Yiftah Ben Aharon, Bakoa (IL)

(73) Assignee: GLUCOME LTD., Yarkona (IL)

( * ) Notice: Subject to any disclaimer, the term of this patent is extended or adjusted under 35 U.S.C. 154(b) by 199 days.

(21) Appl. No.: 14/071,744

(22) Filed: Nov. 5, 2013

(65) Prior Publication Data
US 2014/0127729 A1    May 8, 2014

Related U.S. Application Data

(60) Provisional application No. 61/722,287, filed on Nov. 5, 2012, provisional application No. 61/778,469, filed on Mar. 13, 2013, provisional application No. 61/819,585, filed on May 5, 2013.

(51) Int. Cl.
*G01N 33/487* (2006.01)
*C12Q 1/54* (2006.01)
*G01N 33/66* (2006.01)

(52) U.S. Cl.
CPC ......... *G01N 33/48771* (2013.01); *C12Q 1/54* (2013.01); *G01N 33/66* (2013.01)

(58) Field of Classification Search
CPC ..... G01N 33/48771; G01N 33/66; C12C 1/54
See application file for complete search history.

(56) References Cited

U.S. PATENT DOCUMENTS

| | | | |
|---|---|---|---|
| 8,226,891 B2* | 7/2012 | Sloan | A61B 5/14532 422/82.02 |
| 2001/0032098 A1 | 10/2001 | Kulkarni | |
| 2003/0117987 A1* | 6/2003 | Brebner | H04B 11/00 370/338 |
| 2006/0014186 A1 | 1/2006 | Hodge et al. | |
| 2007/0093717 A1 | 4/2007 | Nagar et al. | |
| 2012/0123222 A1* | 5/2012 | Chen | A61B 5/14532 600/301 |
| 2012/0266251 A1 | 10/2012 | Birtwhistle et al. | |
| 2013/0076533 A1 | 3/2013 | Moran | |
| 2013/0110516 A1* | 5/2013 | Abulhaj | G10L 21/00 704/274 |
| 2013/0197320 A1* | 8/2013 | Albert | A61B 5/02055 600/301 |
| 2013/0346008 A1 | 12/2013 | Bulea | |
| 2014/0019139 A1* | 1/2014 | Abulhaj | A61B 5/14532 704/270 |
| 2014/0376762 A1* | 12/2014 | Lipman | A61B 5/1411 381/365 |
| 2015/0068924 A1* | 3/2015 | Choi | A61B 5/14532 205/782 |

* cited by examiner

*Primary Examiner* — Sam P Siefke
(74) *Attorney, Agent, or Firm* — Yagod Morris & Associates

(57) ABSTRACT

A glucometer is provided, comprising a reader configured to analyze a blood sample, a transmitter configured to wirelessly transmit data, encoded within an audio signal, regarding results of the analysis, and a controller configured to facilitate the encoding.

10 Claims, 10 Drawing Sheets

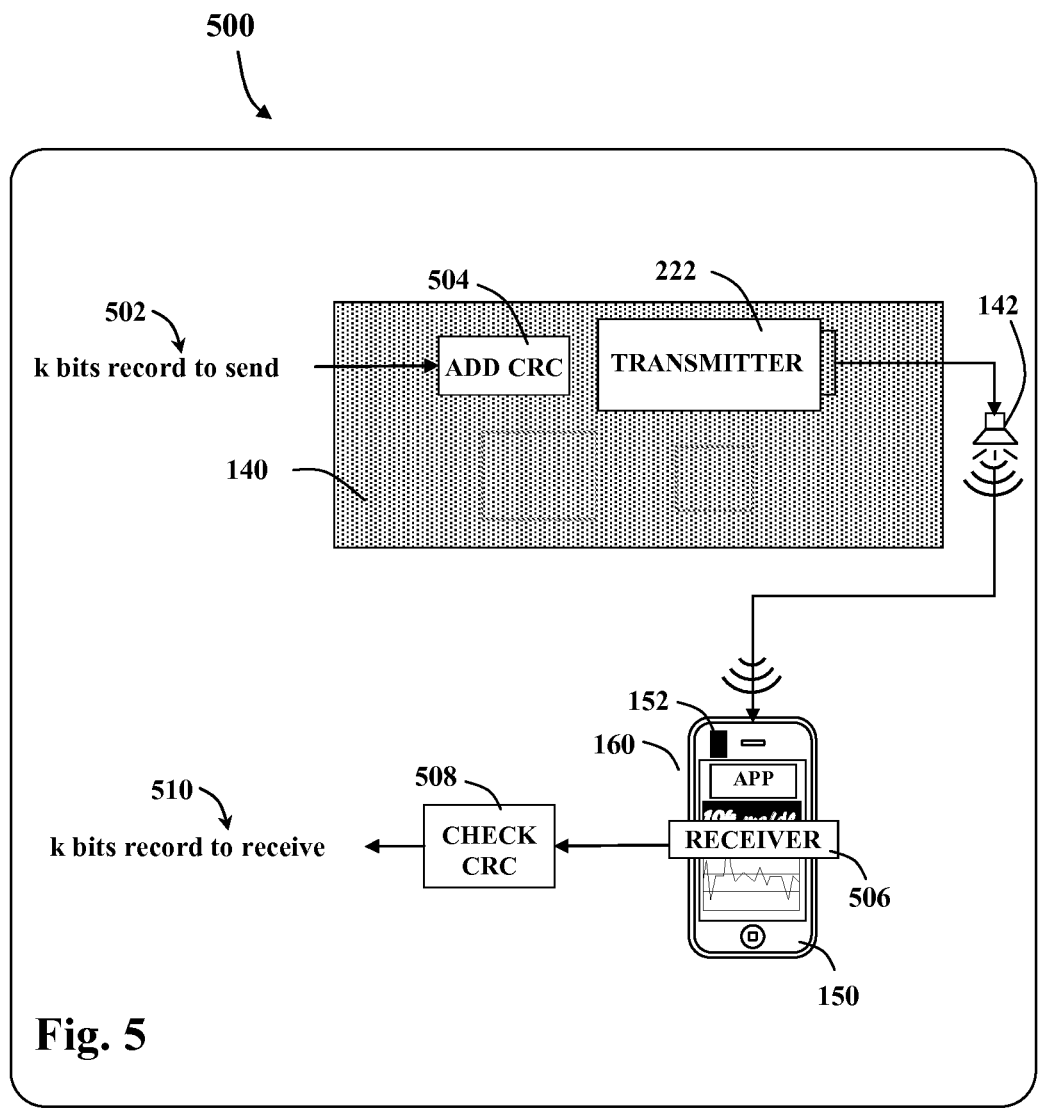

METHOD FOR COLLECTING MEDICAL DATA AND ASSOCIATED SYSTEM

CROSS-REFERENCE TO RELATED APPLICATIONS

This application claims the benefit of priority from U.S. Provisional Patent Application No. 61/722,287, filed Nov. 5, 2012, U.S. Provisional Patent Application No. 61/778,469, filed Mar. 13, 2013, and U.S. Provisional Patent Application No. 61/819,585, filed May 5, 2013, the contents of which are incorporated by reference in their entirety.

FIELD OF THE INVENTION

The disclosure herein relates to the collection and management of medical data of diabetic patients. In particular, the disclosure relates to the transmission of collected blood glucose level information from a glucometer to a remote computing device, such as a mobile phone.

BACKGROUND OF THE INVENTION

Diabetes is a metabolic disease (metabolism) characterized by high blood sugar, also called glucose, resulting from disruption of producing or properly using insulin. Insulin is a needed hormone to convert sugar, starches and other food during digestion, providing the human body's key source of energy.

The blood glucose level or the blood sugar concentration is the amount of glucose (sugar) present in the blood of a human or animal. The body naturally tightly regulates blood glucose levels, while the mean normal blood glucose level in humans is about 72 mg/dL (milligrams/deciliter); however, this level fluctuates throughout the day. Blood sugar levels outside the normal range may be an indicator of a medical condition.

More than 18.2 million people (or 6.3 percent of the population) in the United States suffer from diabetes. Diabetes can cause serious health complications including heart disease, blindness, kidney failure, and lower-extremity amputations. These complications may be avoided through effective and efficient balance of sugar levels. The usage of a glucometer (also called a glucose meter) may be an essential tool for reaching an optimal balance of blood sugar.

Glucometers are commonly used by diabetic patients for self-monitoring of blood glucose levels (and balancing these levels through the use of medication, diet and physical exercise). Even though, self-monitoring of blood glucose is critical for the long-term well-being of diabetic patients, many patients do not adhere to their prescribed self-monitoring due to a combination of physiological and psychological barriers.

Many glucometers use an electrochemical method, based on test media such as test strips. Test strips are a consumable element containing chemicals that react with glucose in a drop of blood used for each measurement. Some glucometers are provided with sophisticated data handling capabilities, but require using a connecting media, such as a cable for transferring the data of the blood glucose level to a computer with diabetes management software to analyze, display the test results or sending it remotely.

Diabetics may monitor their own glucose level using a glucometer. Making such data accessible to a remote health care professional or a caregiver is facilitated if the glucometer is connected to a computer.

It may further be noted that transmission of medical data to remote care givers may be facilitated by a wired or wireless Internet connection in the home, using a USB cable connection, for example. However, collecting the glucose level data and transmitting is more complicated when a user is outside of his home. For example, the user may be a child at school, or a patient on travel. Unless the user has access to a wired or wireless internet connection, a glucometer cannot transmit recorded glucose levels results to his physician or caregiver.

Moreover, a remote computing device that the user may have on hand, such as the user's cell phone, is not able to cooperate with a glucometer, particularly where the remote computing device is configured as a USB slave and the glucometer requires cooperation with a computer that is configured as a USB master.

Although diabetes is a chronic condition that can have serious consequences, with careful attention to blood sugar control, while using appropriately configured remote communication helping blood glucose level monitoring, many of the problems associated with the disease of diabetes may be avoided.

There is therefore a need, for remote self-monitoring of blood glucose level, with the ability to transfer the necessary measured data to a health care professional and/or caregiver.

SUMMARY OF THE INVENTION

The disclosure herein relates to the collection and management of medical data related to diabetic patients. In particular, the disclosure relates to the transferring of collected blood glucose data over an audio-based channel, for example a wireless one, which may be useful for medical assessment and care of an individual suffering from diabetes.

It is an advantage of the current disclosure that it may improve blood glucose level monitoring and enable users' on-the-go to monitor their diabetes and transmit the results to their physicians, to their parents or other care givers. Furthermore, the system described herein may provide a more reliable system for logging diabetes related medical data.

Aspects of the disclosure present a system for collecting blood glucose level information and transmitting the collected data over a wireless audio-based channel for further analysis and storage. The glucometer measures glucose level of a user, using a test medium and a media reader component of a glucometer and structures the measurement into a record by the data processing unit of the device. The glucometer transmits the measurements through the transmitter unit, for example over a wireless audio based channel, to a remote computing device, such as a mobile phone. A pre-installed application may present the results, history data and additional medical assessments and further transmit the measured data to a list of recipients such as physicians, parents, other care givers, to a remote repository for storage or the like.

Optionally, the glucometer and the remote computing device may communicate using protocols such as audio signaling, ultrasonic signaling, infrared communication, BLUETOOTH (i.e., one or more wireless technologies for exchanging distances over short distances using short-wavelength radio transmissions in the ISM band from 2400-2480 MHz as per the standards defined by the Bluetooth Special Interest Group), NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum), WI-FI (i.e., one or more wireless local area network products that are based on the Institute of Electrical and Electronic Engineers' 802.11 standards), ZIGBEE (i.e., one or more of a suite of high level communication protocols used to create personal area networks built from small, low-power digital radios based on the Institute of Electrical and Electronic Engineers' 802.15 standard) or the like.

In some wireless audio based systems, the glucose level medical records may be communicated at a variety of audio frequency levels, where one combination of audio frequencies may represent a '1' bit, and another combination of audio frequencies may represent a '0' bit. Accordingly, a synchronization string combination may be attached before the record data, while a cyclic redundancy check (CRC) data block may be appended to the record data, for error detection of the transmission. The system may include: at least one glucometer for use in measuring of at least one subject; at least one media reader unit for obtaining at least a first glucose level medical record from the at least one test medium; at least one transmitter unit for transmitting measured glucose level record; at least one remote computing device for receiving at least one glucose level record using a wireless audio based channel; and a display mechanism in the remote computing device via which the glucose level records may be accessed.

In general, the glucometer may have no display, and may be unable to display the measured data. According to some modifications, the glucometer may have means to be directly connected to an external output unit, such as a computer, a monitor, a telephone, a tablet, an e-reader device, a handheld display device, or the like.

According to various embodiments, the glucometer may comprise at least one data processor unit, at least one media reader unit, at least one transmitter unit and at least one power source unit.

Optionally, the glucometer monitor may further comprise at least one memory unit, at least one mini/micro USB port and a rechargeable battery as a power source.

Additionally or alternatively, the mini/micro USB port may be used to recharge the rechargeable battery and/or optionally as an output mechanism operable to upload measured glucose medical records stored locally, to a central repository.

It may be noted that in order to implement the methods or systems of the disclosure, various tasks may be performed or completed manually, automatically, or combinations thereof. Moreover, according to selected instrumentation and equipment of particular embodiments of the methods or systems of the disclosure, some tasks may be implemented by hardware, software, firmware or combinations thereof using an operating system. For example, hardware may be implemented as a chip or a circuit such as an ASIC, integrated circuit or the like. As software, selected tasks according to embodiments of the disclosure may be implemented as a plurality of software instructions being executed by a computing device using any suitable operating system.

In various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard-disk, flash-drive, removable media or the like, for storing instructions and/or data. Optionally, a network connection may additionally or alternatively be provided. User interface devices may be provided such as visual displays, audio output devices, tactile outputs and the like. Furthermore, as required user input devices may be provided such as keyboards, cameras, microphones, accelerometers, motion detectors or pointing devices such as mice, roller balls, touch pads, touch sensitive screens or the like.

According to one aspect of the presently disclosed subject matter, there is provided a glucometer comprising:
  a reader configured to analyze a blood sample;
  a transmitter configured to wirelessly transmit data, encoded within an audio signal, regarding results of the analysis; and
  a controller configured to facilitate the encoding.

It will be appreciated that an audio signal is a mechanical wave, such as a sound wave or the like, comprising an oscillation of pressure which is transmitted through a physical medium such as air, water, or solid metal for example. As used herein, the term 'audio signal' is not limited to sound within the range of human hearing but may include ultrasonic waves, infrasonic waves or the like which create effects in a medium which are detectable at a distance by a suitable sensor such as a microphone or the like. As described herein, audio signals may be used to carry a data communication.

The audio signal may be outside the range of human audible frequencies, or it may be within it.

The audio signal may be transmitted at a frequency detectable by at least one microphone associated with a remote computing device. The at least one microphone may be selected from at least one of a group consisting of: an electromagnetic induction microphone, a dynamic microphone, a capacitance change microphone, a piezoelectric generation microphone, a light modulation microphone, a MEMS microphone, and combinations thereof.

The transmitter may be configured to transmit sounds of different frequencies to indicate different values of the encoded data wherein, e.g., for each of the values of the encoded data, the audio signal comprises at least one of a set of frequencies. Each member of the set may correspond to an associated value of the encoded data.

The values may be coded as binary data, or non-binary data, such as decimal, octal, hexadecimal, for example based on the frequency of the sound.

The transmitter may be configured to transmit a synchronization string before transmitting the data.

The transmitter may be configured to transmit one or more of an error-detection code (such as a cyclic redundancy check) and an error-correction code with the data.

The transmitter may be configured to retransmit the data until a predefined event occurs. The pre-defined event may be the removal of a test medium from the glucometer, activation of a button or similar switch on the glucometer, and/or expiration of a timer or counter.

The reader may be configured to analyze the glucose level when the blood sample is disposed on a test medium.

The transmitter may be further configured to transmit data regarding the status of one or more aspects of the glucometer, for example, the battery status.

The reader may be configured to analyze the blood sample when disposed on a test medium, wherein the data regarding the status of one or more aspects of the glucometer comprises information regarding the test medium, such as calibration information, information regarding to make/model of the test medium, etc.

The controller may be further configured to direct operation of the reader and the transmitter.

According to another aspect of the presently disclosed subject matter, there is provided a method of measuring a glucose level in a blood sample, the method comprising:
providing a glucometer comprising a reader configured to analyze a blood sample, and a transmitter configured to transmit data, encoded within an audio signal, regarding results of the analysis;
analyzing of the blood sample by the reader; and
transmitting, by the transmitter, data regarding results of the analysis as a wireless audio signal.

The method may further comprise:
receiving and decoding, by a remote computing device, the audio signal; and
displaying, by the remote computing device, the data.

The method may further comprise calculating, by the remote computing device and based on the data, the glucose level. In this case the data may comprise raw data which is the result of the analysis.

The method may further comprise calculating, by the glucometer, the glucose level, the data comprising the glucose level.

According to a further aspect of the presently disclosed subject matter, there is provided a glucometer comprising:
a reader configured to analyze a blood sample;
a transmitter configured to wirelessly transmit data regarding results of the analysis; and
a controller configured to facilitate operation of the glucometer;
wherein the glucometer is free of a visual data presentation means configured to present the data to a user.

All the elements of the glucometer may be contained within a casing.

The controller may be configured to direct operation of the reader and the transmitter.

The glucometer may be free of visual data presentation means configured to present data using alphanumeric characters.

The glucometer may be free of visual data presentation means configured to present data graphically.

The glucometer may be free of visual data presentation means configured to indicate that the level of glucose in the blood sample is no less than a predetermined level.

The glucometer may be free of visual data presentation means configured to indicate that the level of glucose in the blood sample is no greater than a predetermined level.

According to a still further aspect of the presently disclosed subject matter, there is provided a glucometer comprising:
a reader configured to analyze a blood sample;
transmitter configured to wirelessly transmit data regarding results of the analysis to a remote computing device; and
a controller configured to facilitate operation of the glucometer;
wherein the glucometer is free of means configured to receive input from the computing device.

The transmitting may be performed as defined by a communications protocol, the glucometer being free of means configured to receive input as defined by the communications protocol.

All the elements of the glucometer may be contained within a casing.

The controller may be configured to direct operation of the reader and the transmitter.

The transmitter may be configured to transmit the data wirelessly.

The communications protocol may define encoding data within a wireless audio signal.

The transmitter may be selected from a group including a radio transmitter, an optical transmitter, an infrared transmitter, a transmitter configured to operate as per IEEE 802.11, a BLUETOOTH (i.e., one or more wireless technologies for exchanging distances over short distances using short-wavelength radio transmissions in the ISM band from 2400-2480 MHz as per the standards defined by the Bluetooth Special Interest Group) transmitter, a near-field communications transmitter, and combinations thereof.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings:

FIG. 5 is an illustration of data integrity checking of a record (CRC based) sent between glucometer and remote computing devices;

DETAILED DESCRIPTION OF THE INVENTION

Figure 1:
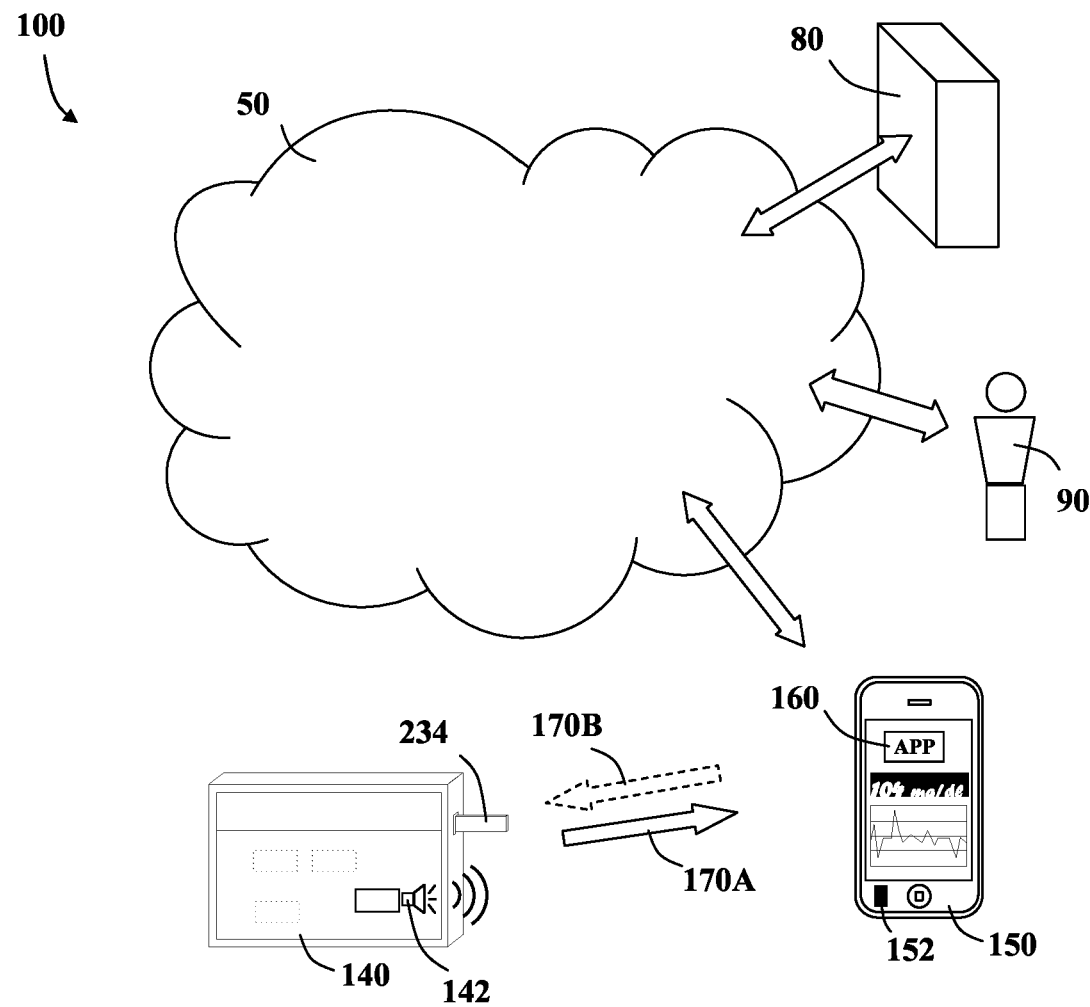
FIG. 1 is a block diagram schematically representing selected components of a system for gathering glucose level data using a plurality of devices.

Aspects of the present disclosure relate to communicating over audio based channel the measured glucose level medical data for diabetic patients, for determining the approximate concentration of glucose in the blood, using a medical measurement device. Transferring the data automatically, over an audio channel to a remote computing device, that in turn may optionally transfer the data to a predefined audience list of professional care givers, parents and the like, is an additional element of the present disclosure, supporting home blood glucose monitoring for example by people with diabetes mellitus or hypoglycemia. Furthermore, related aspects include a medical measurement device without a display, as well as a medical measurement device which is configured to one-way communication, i.e., it is designed to transmit messages using a data protocol, but is not provided with any means configured to receive such or similar messages.

It is noted that the systems and methods of the disclosure herein may not be limited in its application to the details of construction and the arrangement of the components or methods set forth in the description or illustrated in the drawings and examples. The systems and methods of the disclosure may be capable of other embodiments or of being practiced or carried out in various ways.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting.

Reference is now made to FIG. 1 showing a block diagram schematically representing selected components incorporated into a distributed system 100 for the gathering and remote management of glucose level data using a plurality of devices.

The distributed system 100 comprises a plurality of devices, such as medical measurement device 140, which may be, e.g., a glucometer, and remote computing device 150 (which may be, e.g., a smartphone or any other suitable device such as a communications device, and which may constitute an output device). The medical measurement device 140 and remote computing device 150 may be in communication through a wireless audio based channel and may further communicate information to remote devices, such as a central repository device 80, through a network 50 (such as internet- or mobile-based) to a recipient list. For example, the medical measurement device 140 may transmit medical data through the remote computing device 150. The data may thereafter be communicated to a remote caregiver 90, e.g., via a computer or handheld device, such as a smartphone.

It will be appreciated that while the present disclosure is largely directed toward examples wherein the medical measurement device 140 is a glucometer, and the medical data measured thereby is glucose level, any device configured to measure medical data may be provided without departing from the spirit and the scope of the present disclosure, mutatis mutandis. For example, the medical measurement device 140 may be or comprise a thermometer, a scale (measuring any one or more or weight, body fat, bone density, and body mass index), a pulmonary edema monitor, and/or be configured to measure blood oxygen level/saturation, heart rate, blood pressure, physical activity (e.g., a pedometer) and/or calories burnt.

It is noted that a user interface for using the remote computing device 150, such as a touch screen or the like, may serve both as input and output devices thereof. Use of a touch screen may allow the screen to be larger without compromising the size of a separate input device such as a key pad. Furthermore, a touch screen input device may be easier to use for the untrained user as it may use easy to interpret icons rather than complicated text based instructions.

Outbound communications channel 170A (the terms "outbound" and "inbound" when used herein with reference to communication between the medical measurement device 140 and the remote computing device 150 are from the point of view of the medical measurement device) may be provided for communication from the medical measurement device 140 to the remote computing device 150, which may be connected to the network directly. According to some optional and non-limiting modifications, an inbound communications channel 170B may be provided for communication from the remote computing device 150 to the medical device 140 such that the devices may be operable to synchronize data with one another.

The outbound communications channel 170A may be, e.g., an audio based communication channel. As such, the medical measurement device 140 may comprise a transmitter 142, such as a speaker configured to transmit an audio signal encoding data regarding the measured medical data (such as, in the case of a glucometer, blood glucose level) for storage, display, or other purpose. The remote computing device 150 thus comprises receiver 152, such as a microphone (e.g., an electromagnetic induction microphone, a dynamic microphone, a capacitance change microphone, a piezoelectric generation microphone, a light modulation microphone, a MEMS microphone, or combinations of the above) configured to receive the signal transmitted by the transmitter 142.

Optionally, the remote computing device 150 may be configured for sending measured medical data stored thereupon to a professional care giver 90 or uploading to a central repository 80 via a computer network 50. Optionally, the devices may communicate using protocols such as BLUETOOTH (i.e., one or more wireless technologies for exchanging distances over short distances using short-wavelength radio transmissions in the ISM band from 2400-2480 MHz as per the standards defined by the Bluetooth Special Interest Group), NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum), WI-FI (i.e., one or more wireless local area network products that are based on the Institute of Electrical and Electronic Engineers' 802.11 standards), or any other suitable protocol.

The remote computing device 150 may be pre-loaded with an application 160, which facilitates, inter alia, locally viewing and/or analyzing the data measured by the medical measurement device 140.

The application 160 may be configured to send information regarding the measured medical data to a pre-defined recipient list. Such a list may include medical professionals, care givers, parents, and the like. It may store data with a time stamp, so that the measurement data may be provided within a historical context. For example, it may be configured, based on the time-stamped data to graphically present multiple results showing how measured data vary over time.

It is noted that the particular architecture and functionality as described hereinafter, by way of example, refer to a one-way communication protocol between the medical measurement device 140 and the remote computing device 150 via the outbound communications channel 170A. By employing only the outbound communications channel 170A, the medical measurement device can be provided without a receiver, thereby lowering its cost.

Optionally, it is assumed that while using a one-way communication protocol the transmission from the medical measurement device 140 may be repeated until a predefined event occurs. This event may be, for example, a test medium being removed from the medical measurement device 140, activation of a button or similar switch on the medical measurement device (in such a case, the application 160 may be configured to indicate to a user when it has successfully received data via the outbound communications channel 170A and/or instruct the user to activate the button/switch), and/or expiration of a timer or counter.

Furthermore, the medical measurement device monitor 140 and the remote computing device 150 may be complementary interdependent modules, each of which relies on the other to perform the required operations it does not itself perform. For example, the medical measurement device 140 may not itself have a display unit and may only measure the medical data and transmit it. This may be done via a wireless signal. Additionally or alternatively, the medical measurement device 140 may connect to the remote computing device 150 via a cable with a mini/micro USB plug.

Figure 2A:
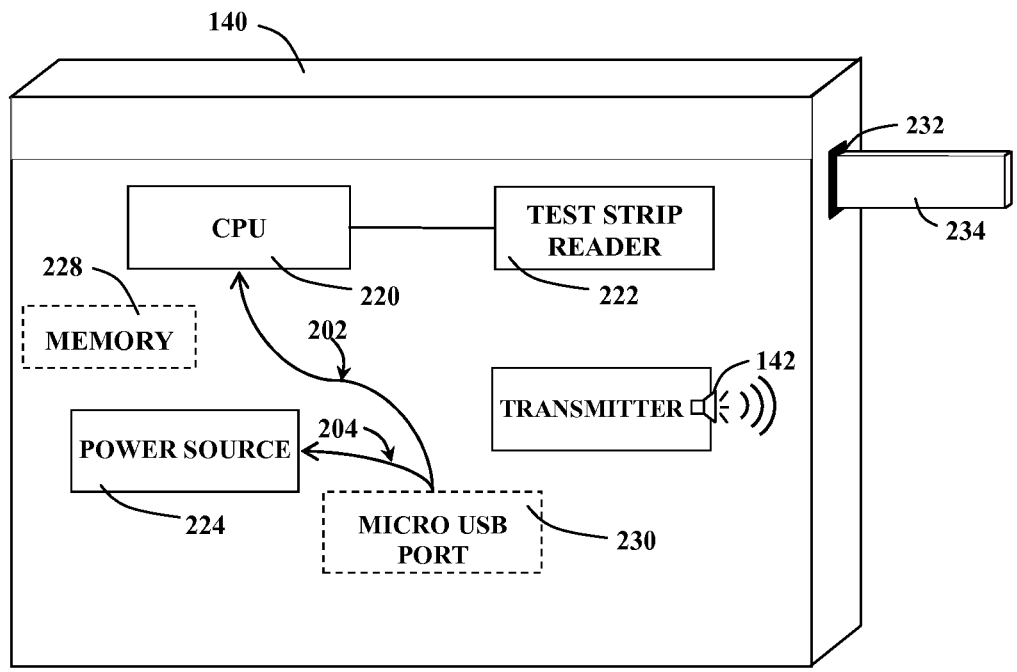
FIG. 2A shows a glucometer incorporating selected elements operable to transmit blood glucose level of a subject, over a wireless audio based channel.

Reference is now made to FIG. 2A where a medical measurement device 140 is shown. In the present example, the medical measurement device 140 is operable to measure and store information regarding a glucose level of a subject. It is also configured to transmit data regarding the information via outbound communications channel 170A. According to some non-limiting modifications, it may be configured to transmit the information as data using a wireless audio based communication protocol. The glucose level and related collected information may be sent to remote devices (not illustrated) used, e.g., by caregivers, parents, etc., or to be stored remotely in a central repository. The transmission may be configured to occur automatically, for example to a pre-defined set of devices, and/or may be initiated manually.

The medical measurement device 140 includes a central processing unit (CPU) 220 constituting a controller, a media reader 222 (for example a test strip reader), a power source 224, a transmitter 142, and a media slot 232. Optionally various other internal elements may be added, such as memory 228 and a micro USB port 230.

As mentioned, the medical measurement device 140 may have a primary function to measure the blood glucose level of a subject. Accordingly, the user may introduce a test medium 234 into the media slot 232 for reading by the media reader 222. Various test media 234 may be used with the medical measurement device 140 as known in the art. For example, test media may be plastic or paper strips impregnated with glucose sensitive chemicals such as glucose oxidase. The strips themselves may have various shapes as required. As known in the art, a subject typically applies a drop of blood to a test medium 234 before introducing the test medium 234 into the medical measurement device 140. The introduction of the test medium 234 into the medical measurement device 140 initiates a process which includes reading the media, calculating the glucose level, and transmitting the glucose level via outbound communications channel 170A to the remote computing device 150.

According to some modifications, the medical measurement device 140 also transmits via outbound communications channel 170A information regarding one or more aspects of itself and/or of the test medium. Such information may include, but is not limited to, the battery level of the medical measurement device 140, calibration data, and/or information regarding specifics of the test medium (model, etc.).

The CPU 220 of the medical measurement device 140 is configured to encode the information before it is transmitted. The encoding may employ binary data, e.g., with two different tones (or ranges of tones) each representing different binary digits, or non-binary, e.g., with several tones (or ranges of tones) being used, each representing a non-binary digit. For example, hexadecimal encoding may be used, with 16 different tones (or ranges of tones) being used, each to represent a digit between $0_{hex}$ and $F_{hex}$. In addition, data compression may be employed, wherein a tone contains more than one bit or data. Alternatively, the information may be sent as an analog signal, for example by "speaking" the information, i.e., by producing sounds mimicking human speech. According to any of the above, the audio signal may be within the range of human audible frequencies, or outside of it.

The CPU 220 is further configured to direct operation of the various elements of the medical measurement device 140, for example the media reader 222 and the transmitter 142.

It will be appreciated that although the CPU 220 is described herein and with reference to the accompanying figures as a single element, it may comprise several elements working together to perform the functions thereof. In addition, some of the functionality thereof may be performed by other elements listed herein (e.g., encoding may be performed by the same element which functions as the transmitter 142). In such a case, the CPU 220 is considered to comprise the elements which perform the functions of the CPU, despite the fact that they are physically located with other elements, mutatis mutandis.

According to some examples of the presently disclosed subject matter, the transmitter 142 comprises an audio-based communicator, such as a speaker, operable to transmit audio signals. The application 160 running on the remote computing device 150 is operable to detect the transmitted audio signals, for example via the receiver 152 thereof. The software application may further be configured to decode the information carried by the audio signals and display the measured glucose level on a display of the remote computing device. Optionally, the application 160 may additionally be configured to enable automatic external communication of the measured glucose level to a pre-defined list of recipients, or manually communicate the measured data to a desired communicator.

Accordingly, according to some examples of the presently disclosed subject matter, the medical measurement device 140 is a closed "black-box" type device with few or no external features, with the exception of, inter alia, the media slot 232 and a battery replacement compartment.

Optionally, the medical measurement device 140 may include an internal memory 228 for storing recorded data which may be accessed later. The medical measurement device may include a micro USB port 230 that may be connected to another device via mini/micro USB cable. The micro USB port may provide dual functionality of charging the power source 224, if the power source is a rechargeable battery and connectivity to the processor 220 for downloading measured information.

It is noted that various graphical user interfaces (GUI) for analyzing the measured glucose information may be used as required, through the application 160 of the remote computing device 150.

According to some modifications of the presently disclosed subject matter, a display is provided in the medical measurement device 140. This display may thus serve as a user interface, for example comprising a touch screen using where appropriate, numerals or text that may be input either via a virtual keypad (not shown) or adjusted using adjustment arrows (not shown), operable to receive user input to configure transmission parameters for sending measured glucose level over the communication channel.

Optionally, the medical measurement device may include a basic structure, with a minimal display functionality of buttons for a user to input data relating to automatic or manual configuration of the transmission, such as time interval for transmission resend and the like.

Figure 2B:
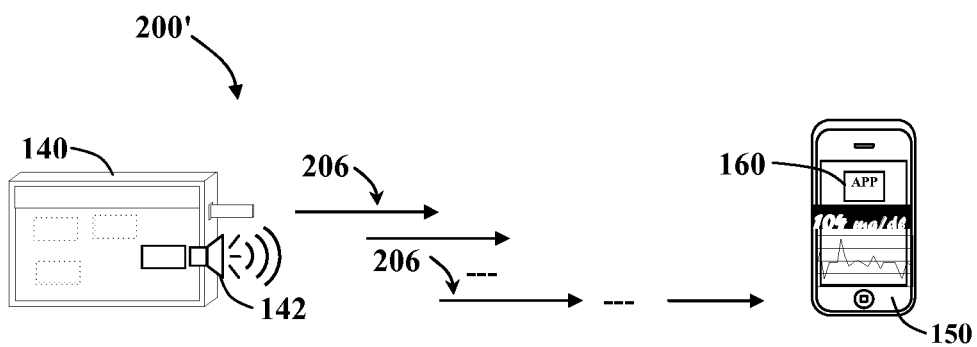
FIG. 2B shows a glucometer configured to communicate with a remote computing device transmitting blood glucose levels of a subject over a wireless audio based channel.

Reference is now made to FIG. 2B, showing a representation of an audio communication system 200' in which a medical measurement device 140 is communicating, using the outbound communications channel 170A described above with reference to FIG. 1, with the remote computing device 150, installed with application 160 for analyzing received glucose data. The glucose level and related collected information may be stored into a record, as described below with reference to FIG. 4, and transmitted to the remote computing device 150 for management and viewing thereof, and optionally for further transmission to caregivers, parents, etc., or to be stored remotely in a central repository.

The medical measurement device 140 may be configured to transmit a record automatically, for example upon introduction of a test medium. Alternatively, or additionally, transmission may be initiated manually by a user, for example via an activation button (not shown) on the device. Transmission signals may be repeated at regular time intervals at a pre-configured rate, for example, every 4 seconds. Accordingly, according to some modifications of the presently disclosed subject matter, the medical measurement device could be provided free of elements which facilitate its receiving input from the remote computing device. This simplification may serve to lower the price of the medical measurement device 140 and/or increase its battery life.

The communication system representation 200' includes the medical measurement device 140 comprising a transmitter 142, a remote computing device 150, constituting a remote output device, such as a smartphone installed with a suitable software application 160 for analyzing the glucose level data, and glucose level data records 206.

It may further be noted that the medical measurement device 140 may be pre-configured to send data signals such as medical content signals or power level notifications at regular time intervals, for example, every 4 seconds. Such data may be received by the associated software application 160 running on the remote computing device 150.

Figure 3:
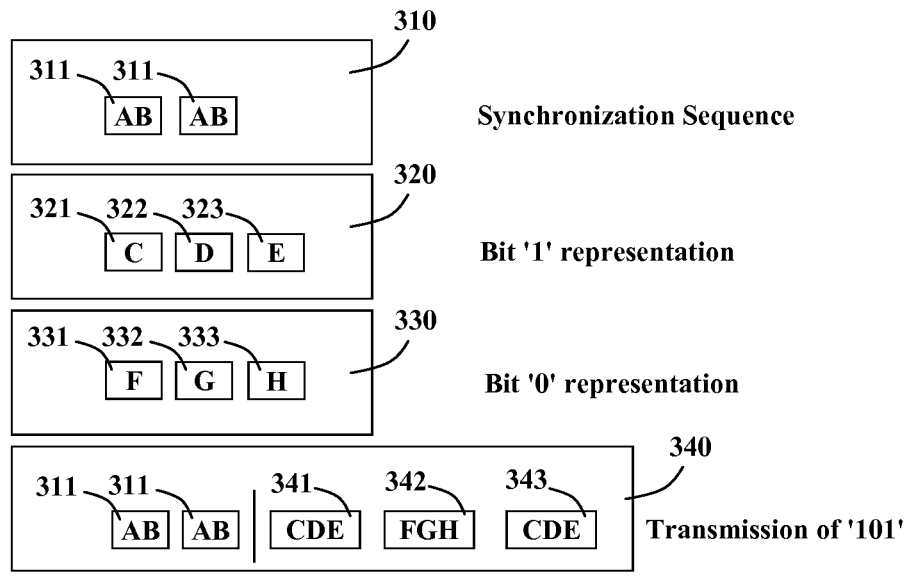
FIG. 3 schematically represents possible elements for creating a record for audio based transmission from a glucometer with a sample transmission.

Reference is now made to FIG. 3, which schematically represents possible elements for creating a record structure for transmission from a medical measurement device, using the wireless audio based communication protocol. The protocol is presented for illustrative purposes only, it will be appreciated that other protocols may occur to those skilled in the art and may be alternatively or additionally utilized.

The communication transmission elements includes a synchronization sequence 310, a bit of '1' representation 320 and a bit of '0' representation 330. These basic elements enable transmitting, for example, a sample level value of 5 ('101' binary sequence), for example, as presented in the 340 representation.

The communication protocol may be based on sending a sequence of '0' (s) and '1' (s) bits for each measurement of information sent, with 'AB' used as a synchronization signal, 'CDE' as an indication for '1' and 'FGH' as an indication for '0', and may use the following frequency levels, for example:

A=4000 Hz; B=4200 Hz; (may be used for synchronization)
C=4400 Hz; D=4600 Hz; E=4800 Hz; (may be used for constructing bit '1')
F=5000 Hz; G=5200 Hz; H=5400 Hz; (may be used for constructing bit '0')

Figure 4A:
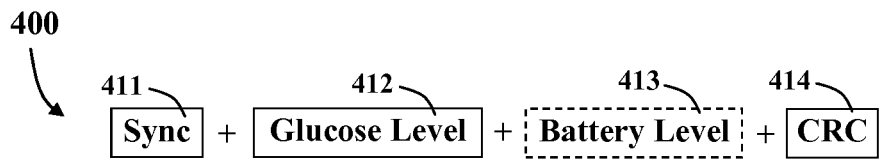
FIG. 4A schematically represents a possible record structure transmitted between glucometer and remote computing device of glucose level data.

Every tone, an 'A', for example, may take 20 milliseconds of transmission. Thus sending a signal of 'AB' may take 40 milliseconds of transmission and a synchronization signal of 'AB'+'AB' may take 80 milliseconds, followed with the actual coded information. Reference is now made to FIG. 4A, representing a possible audio communication transmission 400 of glucose level measurement information from the medical measurement device to a remote computing device, such as a mobile device, for example. The transmission starts with a synchronization signal 411 and ends with a cyclic redundancy check (CRC) 414, an error detection code for detecting errors in the transmitted data.

It may be noted that, according to some examples, the transmission is of one-way communication. As no acknowledgement signal may be sent back when one-way communication is used, it may be useful to send the data signal, for example including glucose level related information repeatedly, e.g., every 4 seconds. According to some modifications, the records and audio communication protocol may, use functionality and commands to acknowledge successful reception of the record by the receiver, configure record timeout, request record resend, etc.

The communication transmission 400 includes a synchronization signal 411, followed by blood glucose level data measurement 412, optionally with battery level data 413 and ended with an encoded CRC error detection sequence 414.

The synchronization signal 411 is of 4T (tones), and may include sending the 'AB' signal twice in a sequence using 2 bits. The blood glucose level measurement 412 may be within a range of 1 to 512 mg/dl of 27T (tones) using 9 bits. The optional battery level information 413 may take a value of 0 to 15 volts, thus of 12T (tones) using 4 bits. This may be completed with CRC error detection using 9 bits. Thus, the whole transmission may need a total of 24 bits. The transmission may also be repetitive, every 4 seconds, for example, and may continue as long as the test medium is inserted in its slot of the medical measurement device.

Transmission of each tone may take 20 milliseconds.

Figure 4B:
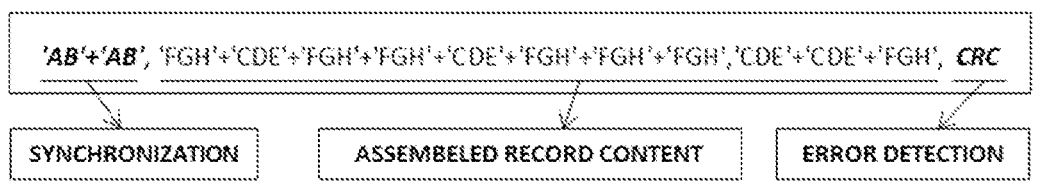
FIG. 4B schematically represents a glucose record sample transmitted between glucometer and remote computing device.

As illustrated in FIG. 4B, in one example, a synchronization signal may be followed by a glucose level value, a battery level value and an error detection signal. A sample transmission of an average glucose level of 72 mg/dl ('01001000') with battery level of 6 ('110') may take the format:

'AB'+'AB','FGH'+'CDE'+'FGH'+'FGH'+'CDE'+
'FGH'+'FGH'+'FGH','CDE'+'CDE'+'FG H', CRC
where the leading string 'AB','AB' represents the synchronization signal, and the terminal value CRC represents the error detection.

The value of the cyclic redundancy check (CRC) for encoding the record by adding a fixed-length check value may be used for error detection and data integrity verification. It may be based on the remainder of a polynomial division or may take a simple format of repeating a value, for a single value record, such as the blood glucose level or sending the sum of the two values, for a record containing the blood glucose level and the battery level, such that in the example above the value 78, being the sum of 72 and 6, may serve as the error detection value.

Reference is now made to FIG. 5 illustrating selected data integrity actions which are indicated of a method for encoding and decoding a record. The record is constructed on the medical measurement device 140 by its CPU 220, after reading the glucose level information from the test medium and verified by a method on the application installed on the remote computing device 150.

According to the method flow, a cyclic redundancy check (CRC) block may be attached at the end of the glucose information record. The record may be composed using the CPU 220 of the medical measurement device 140, resulting in a record having a length of k bits (step 502). This record may include synchronization signal, followed with the measured blood glucose level by the media reader 222 of the medical measurement device 140. Optionally, the battery level may be added to the record. After assembly of the record for sending, a short block of check data, having possibly 9 bits, may be attached at the end of the constructed record (step 504). The record may repeatedly be sent from the medical measurement device transmitter 226 and speaker 142 of the medical measurement device 140, over a wireless audio based channel to the remote computing device 150, at preconfigured time intervals, for example every 4 seconds. The record may be received by the communicator 160 receiver component 506, to enable decoding the attached data block by the application 160, for error detection and correction purposes. For example, a cyclic redundancy check may be used for error detection, and error correction codes (for example by including parity data) may be used for error correction. Once received, the information is decoded, using the attached CRC string to validate the record content (step 508), with a possible output of a record having a length of k bits 510, if the record was properly received.

It may be noted, that the form of cyclic redundancy check (CRC) may apply a customized verification of data integrity, such as attaching the actual transmitted value, if only the blood glucose level is sent, or the sum of the measured glucose level and the battery level, if both values are send.

Figure 6A:
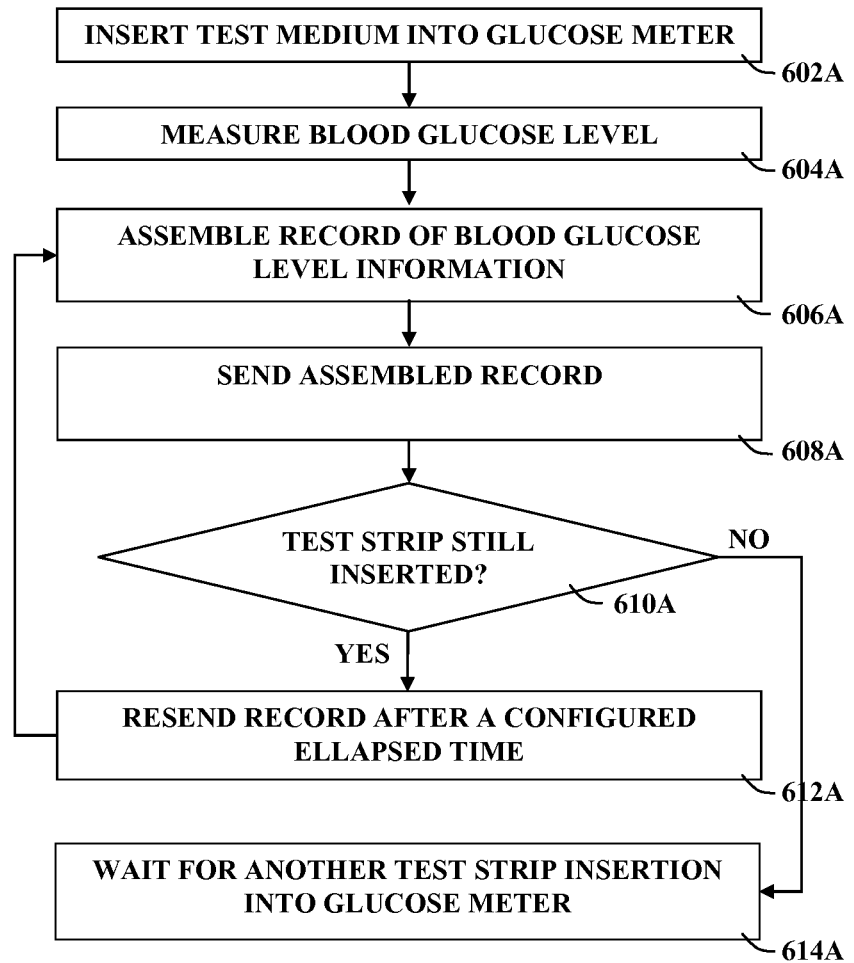
FIGS. 6A through 6D show simplified flowcharts of methods of using a glucometer for gathering and transmitting glucose level data, over a wireless audio based channel.

Referring to the flowchart of FIG. 6A selected actions are indicated of a method for transmitting blood glucose level measured data and related information from the medical measurement device 140 to a remote computing device 150, such as a mobile device installed with a pre-installed application 160. The transmission of the glucose measured level data may be communicated over a wireless audio channel-based system as described hereinabove. Alternatively, or additionally, the outbound communications channel 170A between the medical measurement device 140 and the remote computing device 150 may use a wireless communication system, a NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) system, and the like.

It may be noted that for any network-based architecture such as audio, WI-FI (i.e., one or more wireless local area network products that are based on the Institute of Electrical and Electronic Engineers' 802.11 standards), Wireless, NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) or the like, the record stream may have the same or similar record structures answering the pre-defined communication protocol definitions, as described hereinabove.

It may further be noted that the assembly of the record may be constructed on the medical measurement device, adding a cyclic redundancy check (CRC) indication for checking record integrity upon arrival of the record on the remote computing device.

Alternatively or additionally the form of cyclic redundancy check (CRC) may apply a customized verification of data integrity, such as repeating the measured glucose level, for decoding on the receiving side.

According to the method, as known in the art, a subject will typically apply a drop of blood to a test medium before introducing the test medium into the appropriate medical measurement device slot (step 602A). The medical measurement device will then measure using the media reader 222 to define the blood glucose level (step 604A), and optionally store the measured blood glucose level locally with appropriate timestamp.

The measured value of blood glucose level may be constructed into a record as described hereinabove of communication protocol details, attaching a CRC value for data integrity and error detection (step 606A). The constructed record may then be sent, over the available wireless audio channel (step 608A). It is noted that the remote computing device may then receive the transmitted signal.

If the test medium is still inserted in its slot of the medical measurement device (step 610A), the transmitter of the medical measurement device may continue to resend the current record at pre-defined time intervals, for example, say, every 4 seconds (step 612A). If the test medium is pulled out, the transmitter of the medical measurement device may move into a holding state, until the next test medium is inserted and measured (step 614A).

Figure 6B:
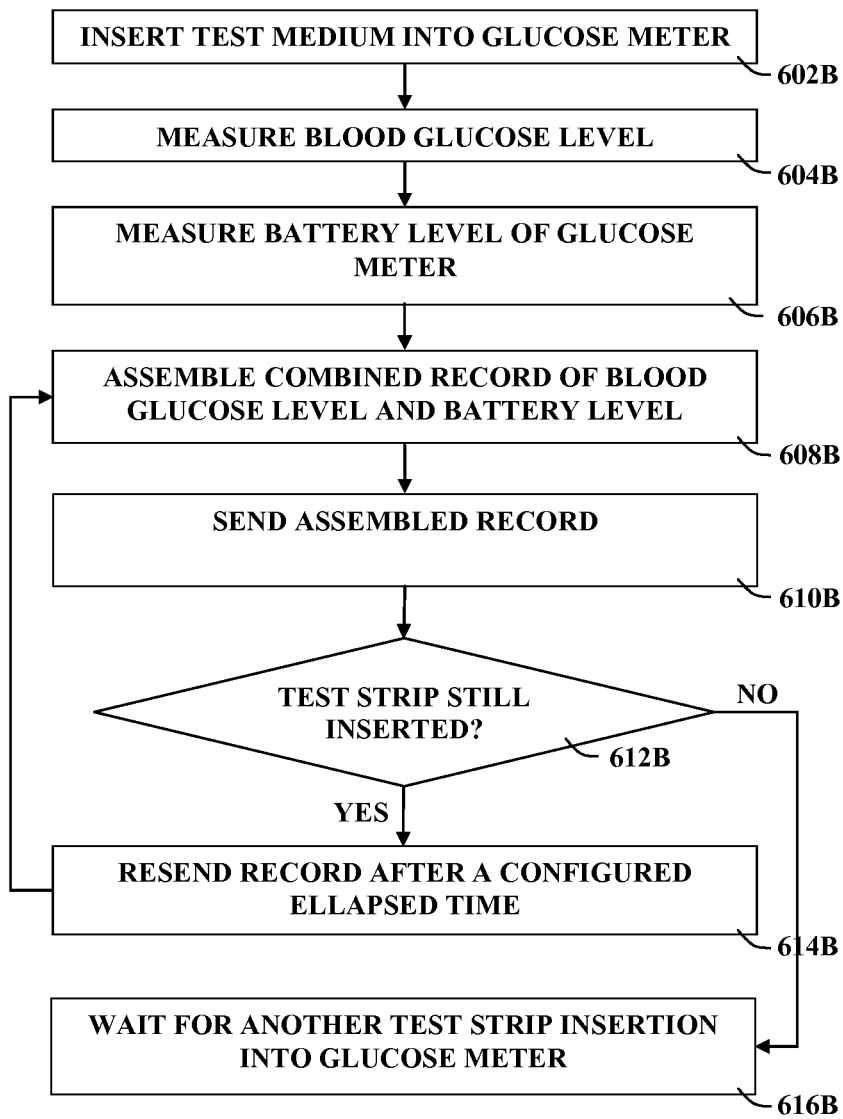

Referring to the flowchart of FIG. 6B selected actions are indicated of a method for transmitting blood glucose level measured data, similar to the method described hereinabove in FIG. 6A, but with adding related battery level information measured at the medical measurement device 140 for sending to a remote computing device 150. The transmission of the blood glucose measured level data and battery level information may be communicated over a wireless audio channel-based system as described hereinabove in FIGS. 3, 4 and 5, to a remote computing device 150, such as a mobile device pre-installed with application 160.

Similarly, a cyclic redundancy check (CRC) may additionally be applied for verifying the data integrity of the received record. The form of cyclic redundancy check (CRC) may apply a customized verification of data integrity, such as attaching the sum of the measured glucose level and the battery level, for decoding on the receiving side. Alternatively, or additionally, the outbound communications channel 170A between the medical measurement device 140 and the remote computing device 150 may use a wireless communication system, a NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) system, and the like.

According to the method, as known in the art, a subject will typically apply a drop of blood to a test medium before introducing the test medium into the appropriate medical measurement device slot (step 602B). The medical measurement device will then measure, using the media reader 222 to define the blood glucose level (step 604B), and further measure the current battery level of the device itself (step 606B), and optionally store the measured blood glucose level and the battery level, locally with appropriate timestamp.

The measured value of blood glucose level combined with the battery level value may be constructed into a record as described hereinabove of communication protocol details, attaching a CRC value for data integrity and error detection (step 608B). The constructed record may then be sent, over the available wireless audio channel to the remote computing device (step 610B). If the test medium is still inserted in its slot of the medical measurement device (step 612B), the transmitter of the medical measurement device will continue to resend the current record every predefined time interval, for example, every 4 seconds (step 614B).

If the test medium is pulled out, the transmitter of the medical measurement device may move into a holding state, until the next test medium is inserted and measured (step 616B).

Figure 6C:
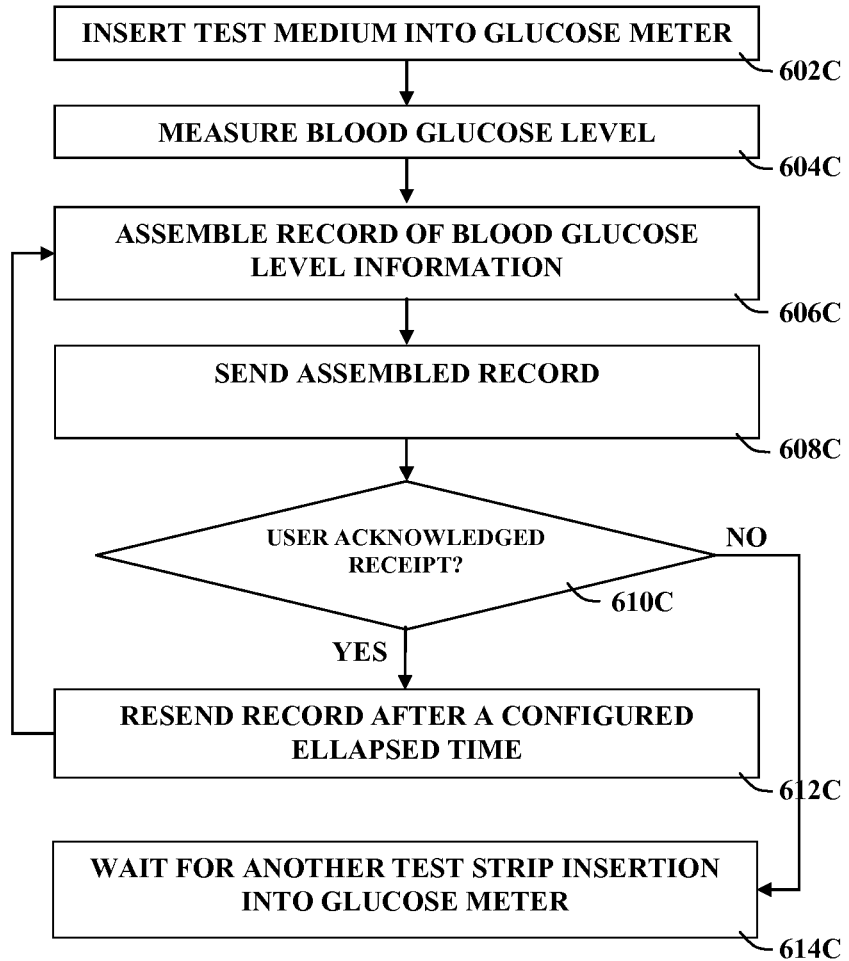

Referring to the flowchart of FIG. 6C, selected actions are indicated of a method for transmitting blood glucose level measured data, similar to the method described hereinabove in FIG. 6A, but with substituting the "decision" of whether or not the user acknowledged that the remote computing device received the information transmitted by the medical measurement device 140. The methods described above with reference to FIGS. 6A through 6C may be useful, for example, wherein the medical measurement device 140 is provided without means to establish an inbounds communications channel 170B.

Figure 6D:
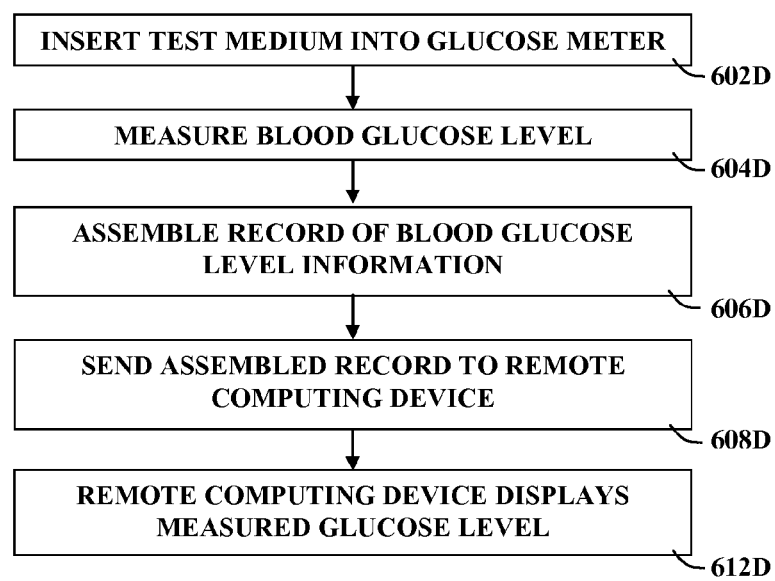

Referring to the flowchart of FIG. 6D, selected actions are indicated of a method for transmitting blood glucose level measured data, similar to the method described hereinabove in FIG. 6A, but without any specified decision regarding resending of data, and with the data being presented by the remote computing device 150. It will be appreciated that this method may be combined with other methods, e.g., it may include a decision step which may necessitate resending of data to the remote computing device 150. It will further be appreciated that such a method facilitates providing a medical measurement device 140 which is free of a data presentation means.

Figure 7A:
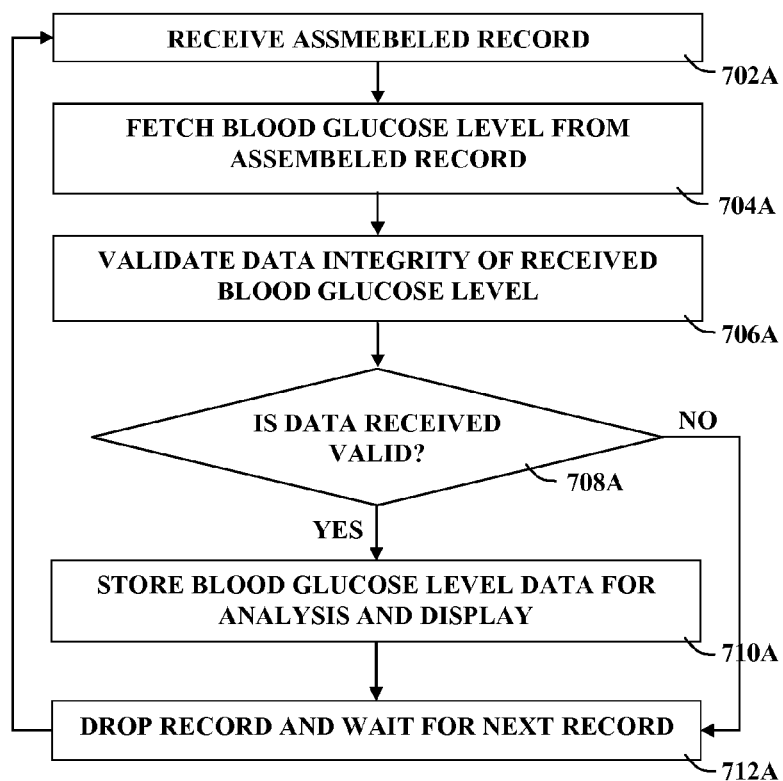
FIG. 7A shows a simplified flowchart of a method of a remote computing device application for receiving glucose level data, over a wireless audio based channel.

Referring to the flowchart of FIG. 7A selected actions are indicated of a method for receiving the signals, such as blood glucose level data, on an output device, such as a computing device running an associated software application method of a remote computing device. The transmission of the glucose measured level data from the medical measurement device may be received over a wireless audio channel using the command elements as described hereinabove. Alternatively, or additionally, the outbound communications channel 170A between the medical measurement device 140 and the remote computing device 150 may use a wireless communication system, a NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) system, and the like.

It may be noted that for any network-based architecture audio, Wireless, NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) or the like, the record stream may have the same or similar record structures answering the pre-defined communication protocol definitions, as described hereinabove with possible adjustment needed for the specific network architecture.

It may further be noted that the disassembly of the received record may contain data integrity validation mechanism, such as a cyclic redundancy check (CRC) indication for validating record integrity by the appropriately designed application of the remote computing device.

Alternatively or additionally the form of cyclic redundancy check (CRC) may contain a customized verification of data integrity, such as repeating the value of the blood glucose level, for performing error detection analysis on the receiving side.

According to the method, the initial step is receiving the assembled record at the communicator application (step 702A). The elements of the record are disassembled, to fetch the blood glucose level (step 704A), thereafter the CRC mechanism for error detection may be used to verify the data integrity of the fetched value (step 706A). If no error is detected in the received record data (step 708A), the blood glucose level may be compared to previously received values (within a specified time, using the timestamp as an indicator) and, thereafter stored for later analysis, immediately displayed, or any other pre-configured activity (step 710A). Thereafter, the record may be dropped waiting for an additional record (step 712A).

It is noted that it is a particular feature of the designed application that the glucose level measurement may be stored in the internal memory of the measurement device or on the remote computing device. The glucose level measurement may be time-stamped when stored, such that the measurement may provide an historical context, providing ability for multiple results to be presented graphically showing how glucose levels vary over time.

Figure 7B:
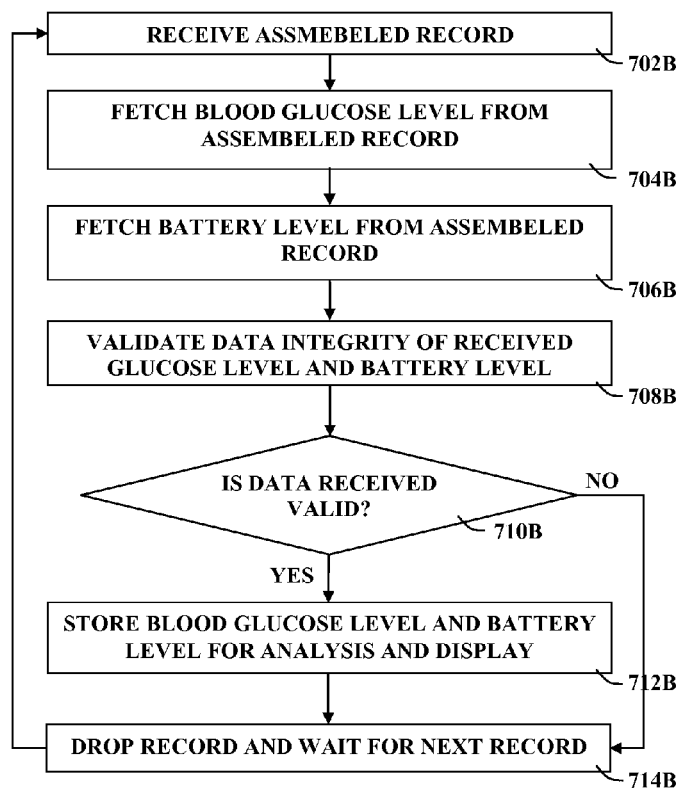
FIG. 7B shows a simplified flowchart of a method of a remote computing device application for receiving glucose and battery level data, over a wireless audio based channel.

Referring to the flowchart of FIG. 7B, selected actions are indicated of an appropriately designed application method of a remote computing device, such as a mobile device for receiving blood glucose level measured data and related information from the medical measurement device. This method is similar to the method described in FIG. 7A, but with a record including related battery level information measured at the medical measurement device.

The transmission of the glucose related measured data may be received over a wireless audio channel-based system using the command elements as described. Alternatively, or additionally, the outbound communications channel 170A between the medical measurement device 140 and the remote computing device 150 may use a wireless communication system, a NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) system, and the like.

It may be noted that for any network-based architecture audio, Wireless, NEAR FIELD COMMUNICATION (i.e., one or more technologies for smartphones and similar devices to establish radio communication with each other by touching them together or bringing them into close proximity, for example based on standards including, but not limited to, ISO/IES 18092 and those defined by the NFC Forum) or the like, the record stream may have the same or similar record structures answering the pre-defined communication protocol definitions, as described hereinabove with possible adjustment needed for the specific network architecture.

It may further be noted that the disassembly of the received record may contain data integrity validation mechanism, such as a cyclic redundancy check (CRC) indication for validating record integrity by the designed application of the remote computing device. Alternatively or additionally the form of cyclic redundancy check (CRC) may contain a customized verification of data integrity, such as sending the sum of the blood glucose level and the battery level of the medical measurement device, for performing error detection analysis.

According to the method, the initial step is receiving the assembled record at the communicator application (step 702B). The elements of the record are disassembled, to enable fetching of the blood glucose level (step 704B), and the battery level information (step 706B), thereafter the CRC mechanism for error detection may be used to verify the data integrity of the fetched values (step 708B). If no error is detected in the received record data (step 710B), the fetched values of blood glucose level and battery level may be compared to previously received values (within a specified time, using the time-stamp as an indicator) and, thereafter stored for later analysis, immediately displayed, or any other pre-configured activity (step 712B), then the record may be dropped waiting for the next record (step 714B).

It is noted that it is a particular feature of the designed application that the glucose level measurement may be stored in the internal memory of the measurement device or on the remote computing device. The glucose level measurement may be time-stamped when stored, such that the measurement may provide an historical context, providing ability for multiple results to be presented graphically showing how glucose levels vary over time.

A particular embodiment is described hereinbelow for illustrative purposes only, but is not limiting and is purely shown by way of example. A medical measurement device 140, having an internal power source, such as an electrochemical cell, measures the blood glucose level using a test medium 234, and transmits the measured glucose level and/or the power level, over an audio-based outbound communications channel 170A to a remote computing device 150 such as a mobile phone or the like. The medical data may be received on the remote computing device 150 by a dedicated application 160, providing ability of presenting results, history data and additional medical assessments and further transmitting the measured data to a list of recipients such as physicians, parents, other care givers, to a remote repository for storage or the like. Optionally, in some embodiments, such a medical measurement device may be a "black box" device with having no output mechanism except for an audio output configured to communicate with a remote computing device running a dedicated software application.

According to some modifications of the presently disclosed subject matter, the medical measurement device 140 is provided without a data presentation means, such as an integral display which is configured to present information regarding the measured medical data to a used, for example graphically (using charts, graphs, etc.) and/or using alphanumeric characters. In addition, the medical measurement device is provided without an integral display (for example an indicator light, LED, etc.) configured to present relative information about the measured medical data, for example if it is above or below a predetermined threshold and/or whether or not it is within a pre-determined range of a previous measurement (or aggregation of a set of previous measurements, e.g., the arithmetic means thereof). Not providing such a display may serve to lower the cost of the unit, and/or to increase its battery life. The remote computing device 150 is configured to receive information regarding measured data via outbound communications channel 170A, and to present it on its display.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A glucometer for measuring a glucose level of a blood sample, comprising:
    a media slot for receiving a test medium;
    a media reader comprising a sensor sensitive to a glucose level of the blood sample disposed on the test medium when introduced into said media slot;
    a transmitter comprising a speaker;
    a processing unit operable to execute instructions; and
    a non-transitory computer-readable memory element for instructions execution by the processing unit, the memory element having stored thereupon:
        instructions to detect the test medium inside said media slot,
        instructions to operate said media reader for reading said test medium inside said media slot,
        instructions to analyze a result of said reading of said media reader and to generate the glucose level of said blood sample disposed on said test medium inside said media slot,
        instructions to produce digital data representing the glucose level of said blood sample, and
        instructions to wirelessly transmit said digital data by said transmitter to a remote computing device, said digital data being encoded within an audio signal,
    wherein said digital data is transmitted repeatedly until said test medium is removed from said media slot.

2. The glucometer according to claim 1, wherein said audio signal is outside the range of human audible frequencies.

3. The glucometer according to claim 1, wherein said audio signal is within the range of human audible frequencies.

4. The glucometer according to claim 1, wherein said audio signal has a frequency selected such that it is detectable by at least one microphone associated with said remote computing device.

5. The glucometer according to claim 1, wherein said instructions to wirelessly transmit comprise instructions to transmit sounds having a set of different frequencies, and said non-transitory computer-readable memory element further comprises instructions to select a frequency from said set of different frequencies to indicate an associated value of the encoded digital data.

6. The glucometer according to claim 5, wherein said non-transitory computer-readable memory element further comprises-instructions to encode said digital data as at least one of binary data and non-binary data.

7. The glucometer according to claim 1, wherein said non-transitory computer-readable memory element further comprises instructions to generate a synchronization string, and said instructions to wirelessly transmit comprise instructions to transmit said synchronization string before transmitting said digital data.

8. The glucometer according to claim 1, wherein said non-transitory computer-readable memory element further comprises instructions to generate one or more of an error-detection code and an error-correction code, and said instructions to wirelessly transmit comprise instructions to transmit said one or more of said error-detection code and said error-correction code with said digital data.

9. The glucometer according to claim 1, wherein said non-transitory computer-readable memory element further comprises instructions to generate data regarding a status of one or more aspects of the glucometer, and said transmitter being further for transmitting instructions to wirelessly transmit comprise instructions to transmit said data regarding the status of one or more aspects of the glucometer.

10. The glucometer according to claim 9, wherein said data regarding the status of one or more aspects of the glucometer comprises information regarding the test medium.

* * * * *

UNITED STATES PATENT AND TRADEMARK OFFICE
CERTIFICATE OF CORRECTION

PATENT NO.        : 9,759,712 B2
APPLICATION NO.   : 14/071744
DATED             : September 12, 2017
INVENTOR(S)       : Dov Moran, Roee Tuval and Yiftah Ben Aharon It is certified that error appears in the above-identified patent and that said Letters Patent is hereby corrected as shown below:

In the Claims

Column 20, Line 42, cancel the text beginning with "9. The glucometer" to and ending "aspects of the glucometer." in Column 20, Line 48, and insert the following claim:

--9. The glucometer according to claim 1, wherein said non-transitory computer-readable memory element further comprises instructions to generate a synchronization string, and said instructions to wirelessly transmit comprise instructions to transmit said synchronization string before transmitting said digital data.--

Signed and Sealed this
Twentieth Day of February, 2018

Andrei Iancu
*Director of the United States Patent and Trademark Office*